(12) United States Patent
Wark et al.

(10) Patent No.: US 7,939,345 B2
(45) Date of Patent: May 10, 2011

(54) VERSATILE SUBSTRATE FOR SPR DETECTION

(75) Inventors: Alastair William Wark, Irvine, CA (US); Hye Jin Lee, Irvine, CA (US); Robert Marcus Corn, Corona del Mar, CA (US); Voula Kodoyianni, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 461 days.

(21) Appl. No.: 12/015,186

(22) Filed: Jan. 16, 2008

(65) Prior Publication Data

US 2008/0113446 A1    May 15, 2008

Related U.S. Application Data

(62) Division of application No. 11/231,626, filed on Sep. 21, 2005, now Pat. No. 7,332,329.

(60) Provisional application No. 60/612,930, filed on Sep. 24, 2004.

(51) Int. Cl.
*G01N 33/553* (2006.01)

(52) U.S. Cl. ........ 436/525; 436/164; 436/172; 436/524; 436/805

(58) Field of Classification Search ...................... None
See application file for complete search history.

(56) References Cited

U.S. PATENT DOCUMENTS

| | | | | |
|---|---|---|---|---|
| 4,877,747 A | * | 10/1989 | Stewart ...................... | 436/525 |
| 5,341,215 A | * | 8/1994 | Seher ......................... | 356/445 |
| 7,352,467 B2 | * | 4/2008 | Chinowsky ................ | 356/445 |

* cited by examiner

*Primary Examiner* — Christopher L Chin
(74) *Attorney, Agent, or Firm* — Boyle Fredrickson, S.C.

(57) ABSTRACT

A substrate for testing a carrier liquid for biomolecules using SPR or other techniques provides a metallic island surrounded by a hydrophobic layer, the islands being a location for the attachment of probe molecules. The hydrophobic layer may also be a dielectric material providing improved sensitivity in SPR imaging.

7 Claims, 5 Drawing Sheets

VERSATILE SUBSTRATE FOR SPR DETECTION

CROSS-REFERENCE TO RELATED APPLICATIONS

This application is a divisional of and claims priority to U.S. application Ser. No. 11/231,626, filed on Sep. 21, 2005 now U.S. Pat. No. 7,332,239, which claims the benefit of U.S. Provisional Application 60/612,930 filed on Sep. 24, 2004.

STATEMENT REGARDING FEDERALLY SPONSORED RESEARCH OR DEVELOPMENT

This invention was made with United States government support awarded by the following agencies: NIH GM059622. The United States has certain rights in this invention.

BACKGROUND OF THE INVENTION

The present invention relates to a substrate suitable for use with surface plasmon resonance (SPR) imaging and other SPR techniques, and in particular to a versatile substrate providing improved sensitivity and ease of use in the identification, detection and quantification of DNA, RNA, proteins, and other biomolecules.

Figure 1:
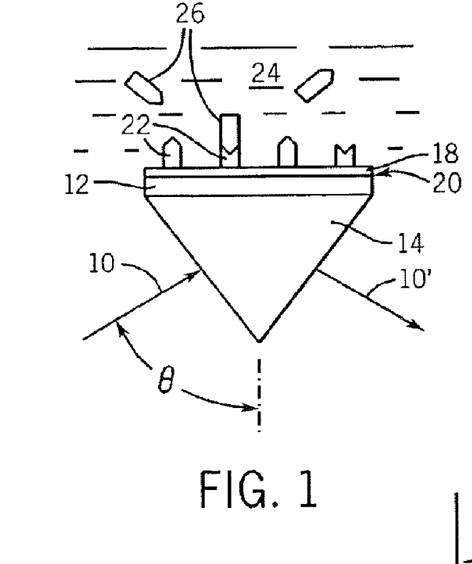
FIG. 1 is a simplified side elevational cross-sectional view of an SPR imaging instrument of the prior art as described above showing the selective reaction of target molecules with probe molecules attached to a substrate.

Referring to FIG. 1 in SPR imaging, a polarized light beam 10 may be directed to the rear side of a transparent substrate 12 at an angle θ as coupled to the transparent substrate 12 by prism 14. The light beam 10 passes through the substrate 12 to reflect off a rear surface of a metallic film 18 adhered to a front surface 20 of the substrate 12. In imaging SPR, the light is received by a camera and the image produced by the camera is analyzed.

The front and exposed surface of the metallic film 18 may have different probe molecules 22 attached to it. These probe molecules 22 may be exposed to a carrier stream 24 containing target molecules 26 which may selectively react with ones of the probe molecules 22 according to a designed experiment.

The intensity of reflected light beam 10' from different points on the rear surface of the metallic film 18 will be dependent on the density of material (probe molecules 22 and target molecules 26) attached to the front side of the metallic film 18. This variation is caused by a change in reflectivity (% R) of the metallic film 18 caused by modification of surface plasmon resonance of the metallic film 18 by the material on the front side of the metallic film.

Figure 2:
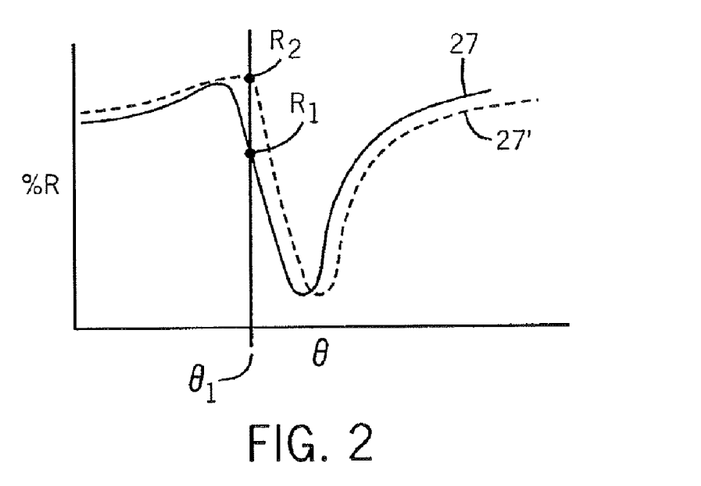
FIG. 2 is a plot of reflectivity as a function of angle for a location on the substrate of FIG. 1 before and after the reaction of the probe molecules with target molecules.

Referring to FIG. 2 for a given angle $\theta_1$, the reflectivity of the rear of the metallic film 18 at any given point will vary from value $R_1$ to value $R_2$ as the reflectivity curve 27 shifts rightward to reflectivity curve 27' with the increase in material attached to the front side of the metallic film 18. A precise measurement of reflectivity R can thus reveal a location of the binding of the target molecules 26. This location, together with the known location of complementary probe molecules 22, can reveal the type of target molecules 26 in the carrier.

SPR imaging normally looks at a difference in reflectivity ($R_1$) of the substrate prior to reaction with the target molecules 26 and in reflectivity ($R_2$) of the substrate after reaction with the target molecules to accentuate the changes caused by the binding of probe molecules 22 and target molecules 26 to reduce baseline variations in reflectivity caused by the probe molecules 22, variations in the metallic film 18 and substrate 12, and changes in the material of the front surface metallic film 18.

SPR imaging delivers sensitive detection of target molecules without the need to label the target molecules, for example, with fluorescent or radioactive materials as is otherwise necessary to detect concentrations of target molecules at particular locations.

BRIEF SUMMARY OF THE INVENTION

The present invention provides a new substrate for imaging SPR and other SPR techniques providing improved sensitivity and/or ease of use.

In one embodiment, the substrate employs a dielectric layer positioned between the substrate and the metallic film to promote "long range" surface plasmon resonance, increasing the sensitivity of reflectivity to concentrations of target molecules.

In one embodiment, the dielectric is hydrophobic and the metallic film is placed in islands on top of the dielectric and surrounded by exposed dielectric. The hydrophobic properties of the surrounding dielectric aid in localizing the probe molecules on the islands of metallic film and minimizing reactions and/or contamination between islands.

Specifically then, the present invention provides a substrate for use in SPR imaging comprising a support surface transparent to analyzing light and a similarly transparent dielectric layer is adhered to this support surface. A metallic film is adhered to at least a portion of the dielectric surface and supports exposed probe molecules which may react in situ with a target molecule. The dielectric layer is selected to promote long-range surface plasmon resonance.

It is an object of at least one embodiment of the invention to provide a substrate for SPR imaging that enhances surface plasmon resonance effects.

The metallic film may be divided into spatially isolated islands.

It is thus another object of at least one embodiment of the invention to provide improved localization of probe molecules.

The dielectric surface material may be hydrophobic.

It is therefore an object of at least one embodiment of the invention to provide improved localization of the reactions between probe molecules and target molecules.

The dielectric material may be a halogenated polymer such as the fluoropolymer, Cytop.

Thus, it is another object of at least one embodiment of the invention to provide a dielectric material that can be uniformly applied in the necessary thickness for desirable dielectric properties, is hydrophobic, transparent at the necessary wavelengths, and resistant to chemical erosion during further manufacturing and/or analysis steps.

More generally the invention provides a support surface having a plurality of islands of metallic film surrounded by a hydrophobic material.

It is therefore an object of at least one embodiment of the invention to provide a general purpose substrate that may be used to conduct multiple reactions with target molecules in a carrier solution with improved reaction localization.

The substrate may be fabricated by coating the support surface with a hydrophobic layer and attaching the metallic film islands on top of that layer.

Thus it is another object of at least one embodiment of the invention to provide a practical manufacturing method for the substrate usable in a variety of applications.

The hydrophobic layer may be applied through a spin coating of a solventized hydrophobic material.

It is therefore another object of at least one embodiment of the invention to provide a technique suitable for obtaining an extremely even thickness of hydrophobic material so as to provide acceptable SPR stability while resisting attack from chemicals that degrade or release other types of hydrophobic materials.

A general object of at least one embodiment of the invention is to provide a substrate suitable for both SPR measurements and other array type detection techniques, for example, those using fluorescence or radioactivity.

These particular objects and advantages may apply to only some embodiments falling within the claims and thus do not define the scope of the invention.

DETAILED DESCRIPTION OF THE INVENTION

Figure 3:
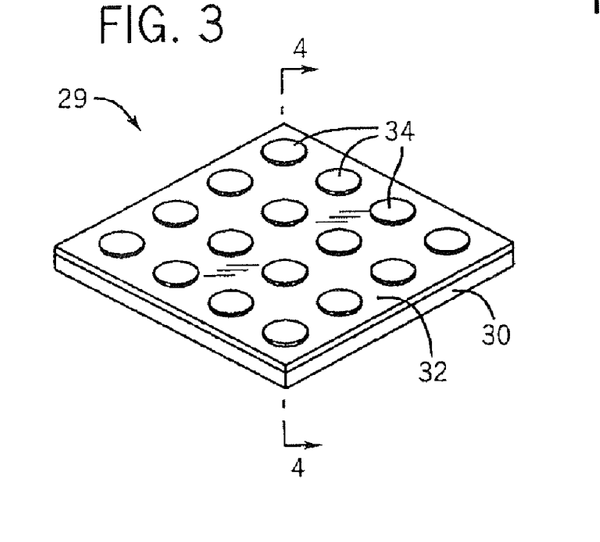
FIG. 3 is a perspective view of a substrate of the present invention showing isolated islands of metallic film surrounded by a hydrophobic dielectric layer attached to a transparent substrate.
Figure 4:
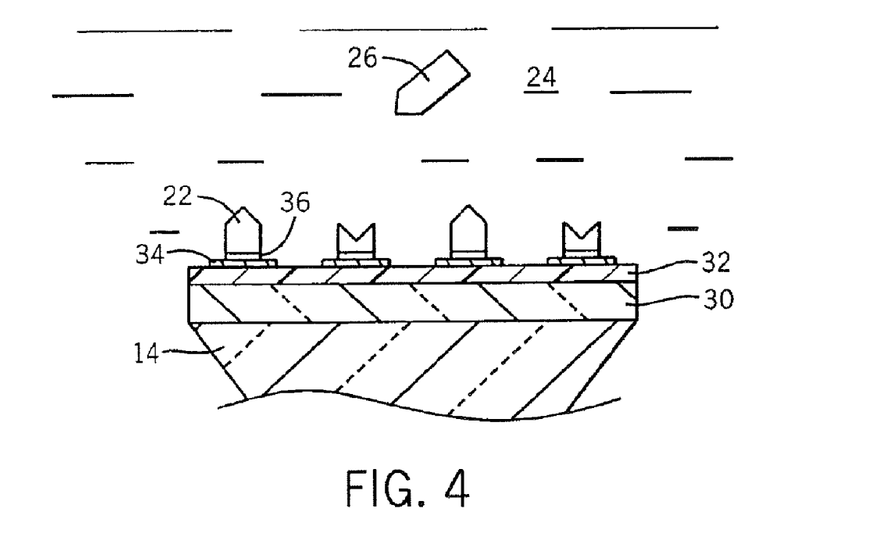
FIG. 4 is a cross-sectional view through the substrate of FIG. 3 as supported by a prism of an SPR instrument and exposed to a carrier solution.

Referring now to FIGS. 3 and 4, the present invention provides substrate 29 having a generally planar support surface 30 of a transparent and chemically inert material preferably an SF 10 glass slide. The rear surface of the support surface 30 may fit against a prism 14 of similar index of refraction in a conventional SPR instrument (not shown). Alternatively, the prism 14 may provide the substrate 29 directly.

The front surface of the support surface 30 is coated with a dielectric layer 32 that has a refractive index similar to that of the aqueous carrier stream 24 used to support target molecules 26. The dielectric layer 32 is desirably substantially transparent at the desired wavelength of the SPR instrument, typically 500-1800 nm and, for example, 814 nm and 1800-5000 nm for infrared SPR.

In the preferred embodiment, the dielectric layer 32 may be approximately 1800 nanometers thick and fabricated of Cytop. Cytop ("cyclized transparent optical polymer") is a copolymerization of perfluoro (alkenyl vinyl ethers) commercially available from Asahi Glass Company and is available in the United States through Bellex International Corporation, Wilmington, Del. The Cytop material designated CTL-809M may be used for spin-coating applications. The Cytop material is preferably spin coated using a 9% by weight solution of Cytop dissolved in a perfluorinated solvent on the SF 10 glass slide. The slides may be baked at 70° for forty minutes and 180 for one hour following the manufacturer's guidelines. Spin coating is a well-understood technique that provides for uniform thickness of viscous materials over a surface.

Other dielectric materials including other fluoropolymers such as Teflon AF may also be used; however, suitable surface smoothness required for imaging can be hard to obtain. Metal halite films such as $AlF_3$ and $MgF_2$ as prepared by vapor deposition provide good optical quality, but are less desirable because they are hydroscopic and the interface between gold and the metal halite layer roughens upon contact with water. Possible dielectric layers are listed in the following table:

| Dielectric layer | Refractive index @ 800 nm | Preparation method | Film Quality | Adhesion Layer Cr | Ti | Dielectric Film solubility |
|---|---|---|---|---|---|---|
| AlF3 | 1.35 | Vapor dep. | Excellent | Medium | Poor | Medium |
| MgF2 | 1.387 | Vapor dep. | Good | Medium | Poor | Medium |
| 80% MgF2 20% BaF2 | 1.403 | Vapor dep. | Excellent | Medium | Poor | Medium |
| BaF2 | 1.4258 | Vapor dep. | Good | Weak | N/A | Medium |
| Cryolite | 1.36 | Vapor dep. | Good | Medium | N/A | High |
| CaF2 | 1.445 | Vapor dep. | Good | Medium | N/A | High |
| Teflon 1600 | 1.31 | Spin coating | Poor | Good | Poor | None |
| PDMS | 1.42 | Spin coating | Poor | V. Poor | N/A | N/A |
| Cytop | 1.34 | Spin coating | Good | Good | Poor | None |

The front surface of the dielectric layer 32 is patterned with metallic film islands 34 (for example, a 32 nanometer gold film) which most simply may be circular islands 34, but which can be arbitrary other shapes as will be understood from the following description. The island 34 may be attached to the dielectric layer 32 by means of an adhesive layer of chromium or titanium approximately 1.0 nanometer thick. The islands 34 and adhesive layer may be prepared using vapor deposition and standard metal mask patterning procedures. For example, a 0.006 inch thick stainless steel mask may be used for the patterning.

The size and density of the islands 34 can be varied. A spot diameter of 1 mm and center to center separation distance of 1.67 mm may be used, however, spots as small as 0.7 mm and with a center to center separation of 1.25 mm may also be used, and there is no practical limit to reducing these sizes to at least 50 microns. The larger sizes allow manual application of probe molecules 22 to the islands 34 typically with less than 100 islands per square centimeter.

Significantly in the preferred embodiment, the islands 34 are separated by exposed dielectric layer 32 which also may be hydrophobic. Although the inventors do not wish to be bound by a particular theory, it is believed that the hydrophobic surface provided by the dielectric layer 32 significantly reduces the attachment of probe molecules 22 or other contaminating materials to the area between the islands 34. This more constant baseline provides an improved reference both for identifying the regions of the islands 34 and in setting thresholds for automatic image analysis and the like.

The dielectric layer 32 may be also used solely for its hydrophobic properties, deposited in a layer too thin for promotion of long range SPR. Cytop, for example, may be applied to the support surface 30 in a thin layer functioning as a hydrophobic surface, but not necessarily as a sensitivity enhancing dielectric, using a 1.5% by weight, or lower, for example 0.375%, dilute solution of Cytop with a spin rate of up to 5,000 rpm.

In contrast, a common hydrophobic surface treatment, silanization, is also possible. In one method of silanization, the support surface 30 is subject to repeated immersions in a solution of Dimethyloctadecyl-chlorosilane followed by oven curing at 110° C. for one hour. It is believed, however, that subsequent surface chemistry needed for many applications of the substrate using solvents such as ETOH can cause desorption of silane molecules from a glass surface allowing them to compete for binding sites with thiol molecules upon the islands 34 thus degrading the quality of the SAM 36 formed.

While the present invention contemplates that the islands 34 will be placed directly on the dielectric layer 32, it would be understood that the benefits of the hydrophobic layer alone may be obtained simply by surrounding islands 34 attached directly to the support surface 30 with a hydrophobic layer that may be screened on.

Upon completion of the dielectric layer 32 and application of the islands 34, the front surface of the islands 34 may be coated with a self-assembled monolayer 36 (SAM). For example, the SAM layer may be an amine-terminated alkanethiol (11-mercaptoundecylamine, MUAM) for example, as is taught in U.S. Pat. No. 5,242,828 hereby incorporated by reference.

The SAM 36 is then followed by linker and then probe molecules 22, as have been described, upon binding with a target molecule 26. Linkers suitable for this application are described in U.S. Pat. No. 6,127,129, and U.S. patent publication 20020044893 and 20030017579 all hereby incorporated by reference. The probe molecules may be snippets or whole molecules of DNA, RNA, proteins, and peptides selected to bond or hybridize with particular target molecules 26 of interest. More generally, the probe molecules can be whole proteins, genes, mRNAs, molecules complimentary to micro RNA, RNA fragments or DNA fragments, peptides or carbohydrates or any molecule that can be immobilized on the gold surface.

The target molecules 26 may be on the surface coats of cells or viruses to allow capture and characterization of cells and viruses.

Generally, the islands 34 provide visual registration of the location of the probe molecules 22, thus allowing hand spotting of the materials of the SAM 36 and probe molecules 22 and an automatic registration of these areas with imaging equipment for automatic spotting. For large sizes of islands 34 with low density, the substrate 29 of the present invention may be prepared on an individual basis by a user having a kit including the substrate 29 and material of the SAM 36 without the need for complex photolithography-type equipment often used for manufacturing arrays of probe molecules. Gold spots surrounded by hydrophobic background can (i) help robotic registration (ii) result in improved probe morphology and (iii) make subsequent computerized image analysis easier.

Figure 10:
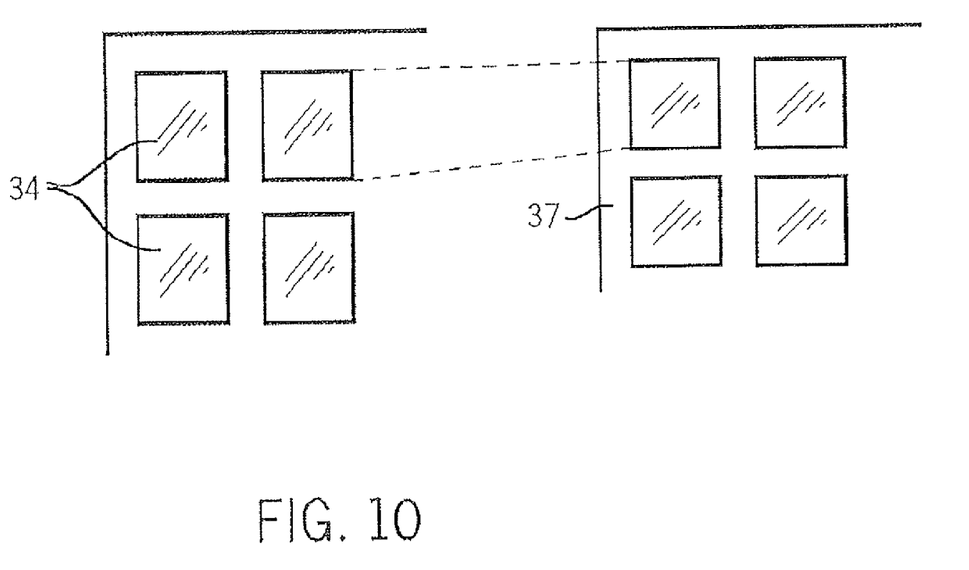
FIG. 10 is a top plan view of substrate of FIG. 3 and its oblique projection as viewed by an SPR machine.

Referring to FIG. 10, the metallic islands 34 may have outlines that are rectangles or ellipses with their long axes extending in the SPR machine along the path of light beam 10, so that when viewed obliquely at the angle θ of the light the outlines of the islands 34 project to a square or circle in an image 37 captured by the SPR machine, respectively, providing improved automatic registration and analysis of the image produced by the SPR machine. Similarly, the islands 34 may have an arbitrary shape that projects to substantially regular polygon having equal width and height.

Figure 5:
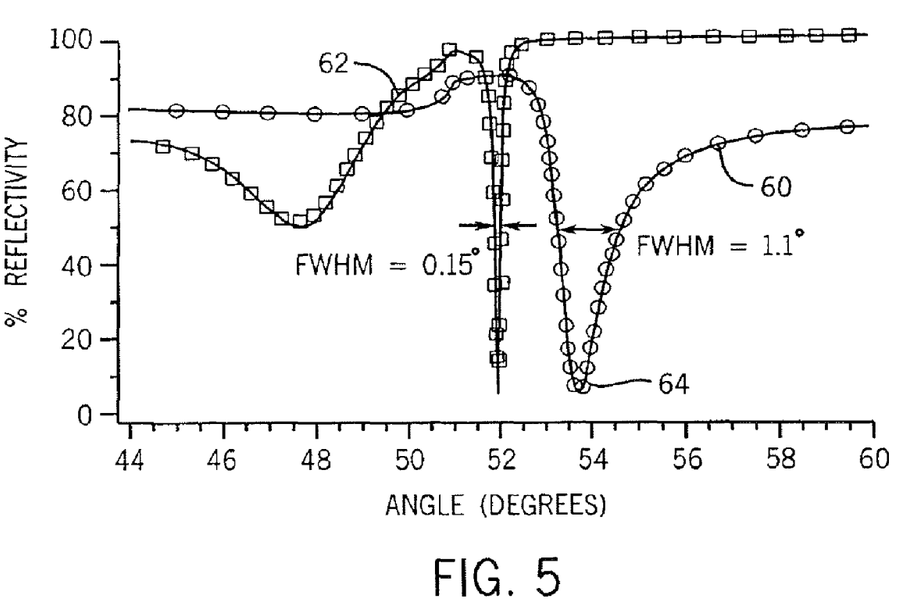
FIG. 5 is two plots of reflectivity vs. angle showing an increase in the sharpness of the reflection curve with the introduction of the dielectric layer of FIGS. 3 and 4.

Referring now to FIG. 5, reflectivity curve 27 using a substrate not having a dielectric layer 32, exhibits a broader reflectivity trough 60 having a full width half maximum (FWHM) measurement of approximately 1.1° of θ in contrast to narrower trough 60 on a theoretical model of a curve of reflectivity for a substrate having a dielectric layer 32 which exhibits a FWHM measurement of approximately 0.15°. This and the following described figures employ a model of the properties of the dielectric and other layers 32 based on n-phase Fresnel calculations well understood in the art.

Figure 6:
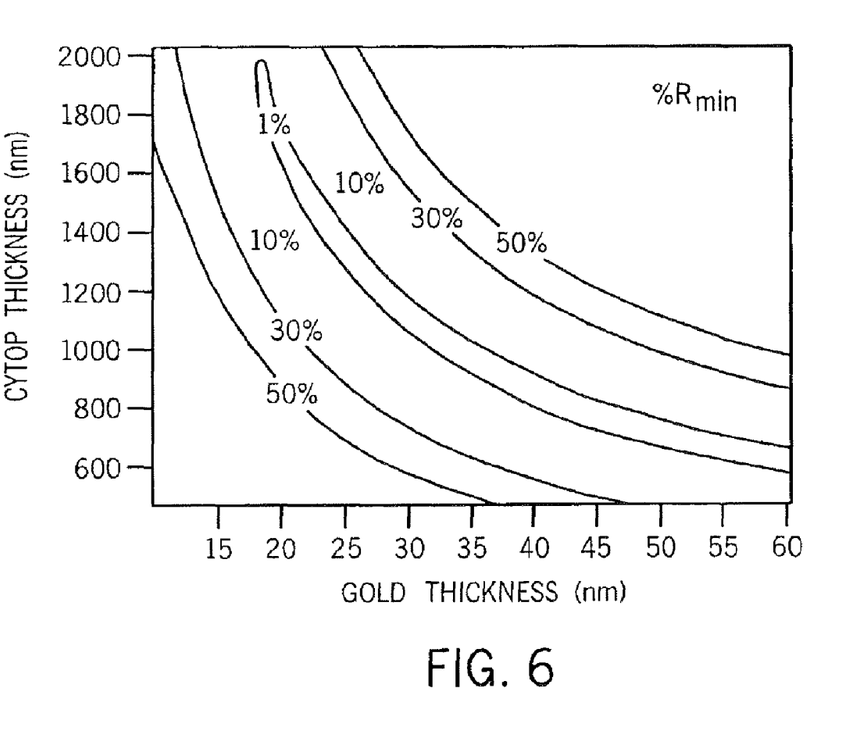
FIG. 6 is a theoretical contour plot of the reflection minimum of the plot of FIG. 5 for a dielectric layer as a function of Cytop dielectric thickness and gold thickness relevant to the selection of dielectric thickness.

The relative thickness of the islands 34 and that of the dielectric layer 32 may be optimized. Referring to FIGS. 5 and 6, one optimization metric is the minimum reflectivity 64 that may be obtained in the presence of combined probe and target molecules. In this figure, a lower value of minimum reflectivity 64 is desired.

Figure 7:
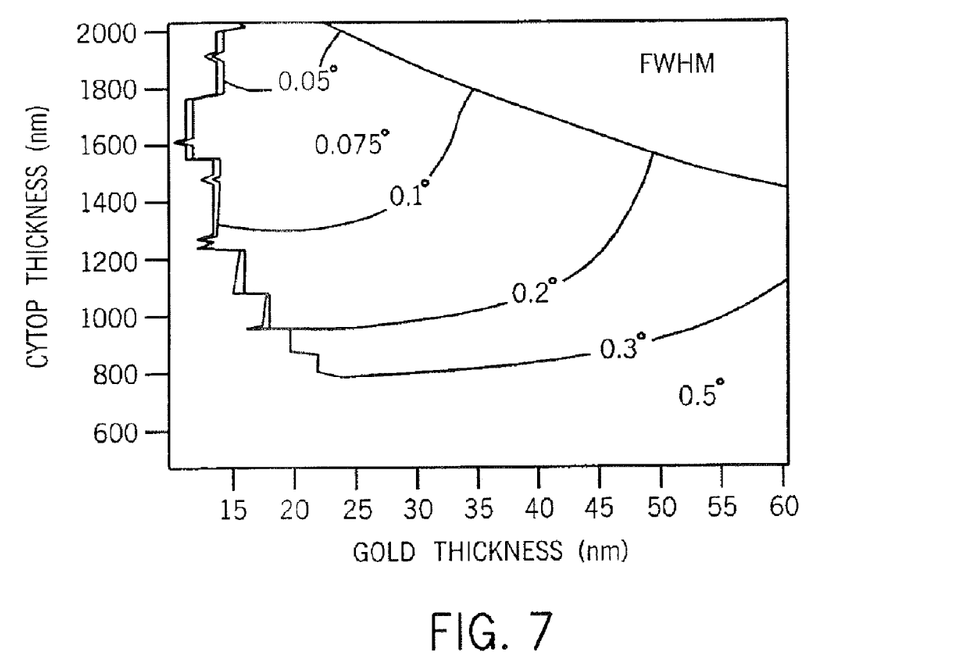
FIG. 7 is a theoretical contour plot showing the relationship between the thickness of a Cytop dielectric and a gold metallic layer as it affects a full width half maximum (FWHM) of the plot of FIG. 5 for a dielectric layer.

Alternatively or in addition, referring to FIGS. 5 and 7, the relative thickness of the dielectric layer 32 and islands 34 may be used to minimize the FWHM value of the trough 62 with smaller values being superior.

Figure 8:
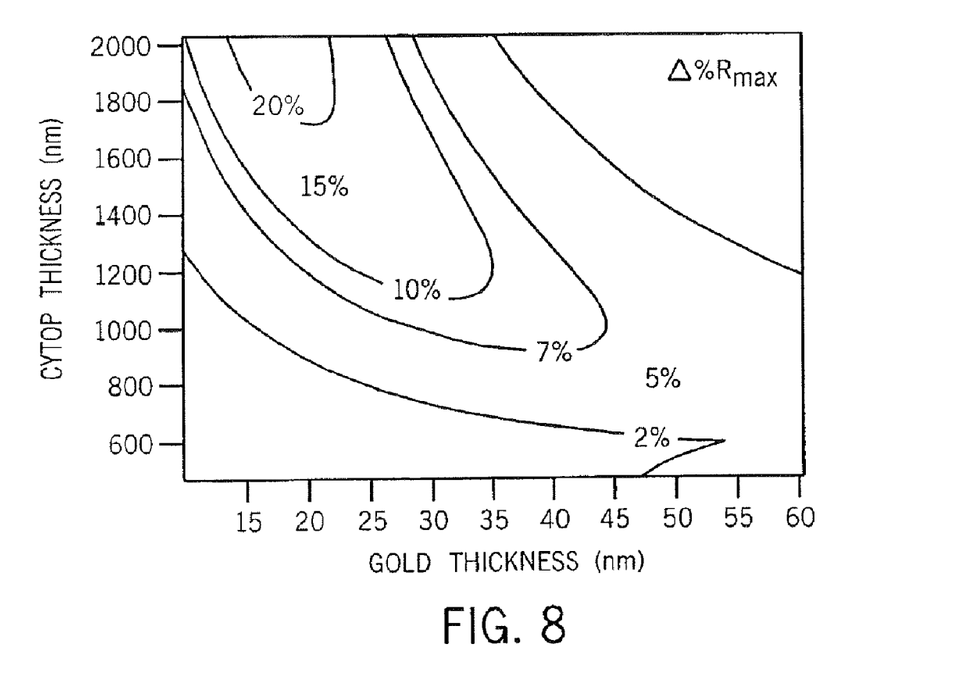
FIG. 8 is a theoretical contour plot of the difference in reflectivity as a function of Cytop thickness and gold thickness relevant to the selection of appropriate dielectric layer thickness.

Referring to FIGS. 5 and 8, generally the goal is to maximize change in reflectivity (A % R) being the difference between values $R_1$ and $R_2$.

Note that with respect to the theoretical predictions of FIG. 8, the support surface 30 of SF 10 glass alone (without a dielectric layer 32) provides approximately a 7% Δ% R value, and therefore for dielectric improvement in SPR sensitivity, at least 1,000 nm Cytop thickness will be indicated although the present invention is not limited to this value provided long range SPR is obtained. On the other hand, when the dielectric layer 32 is used solely for its hydrophobic properties, extremely thin layers of dielectric material may be desired, e.g., less than 20 nm but normally greater than 3 nm.

Figure 9:
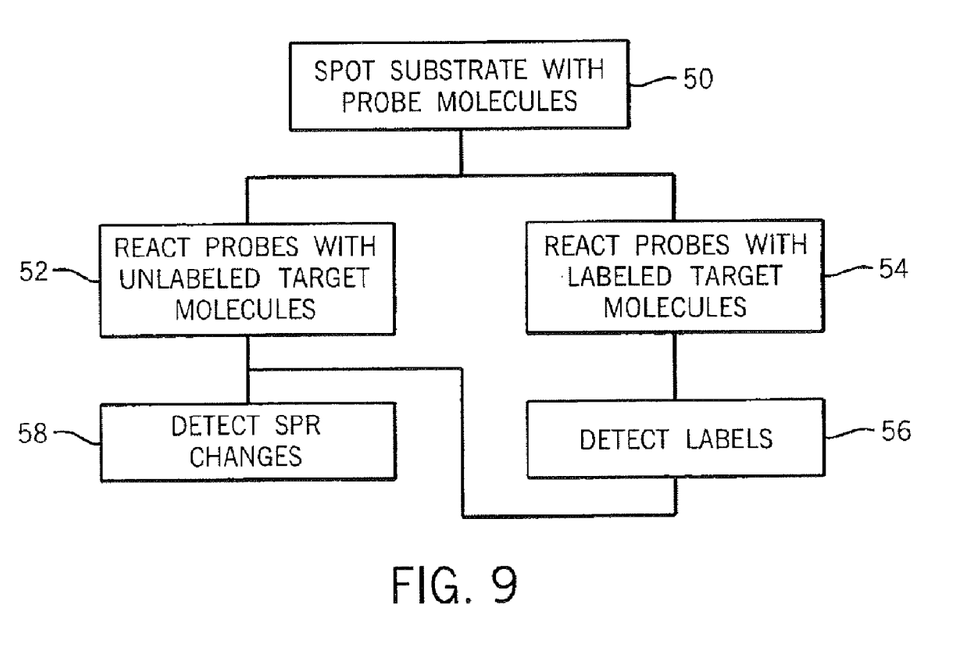
FIG. 9 is a flow chart showing steps of using the present invention in analysis of biomolecules.

Referring now to FIGS. 3, 4 and 9, the substrate 29 of the present invention may find use in areas outside of SPR imaging including use with standard fluoroscopy or radioactive assaying equipment or in a novel combination of SPR and fluoroscopy and/or radioactive tagging.

As indicated by process box 50, probe molecules 22 may be spotted onto the gold surface of islands 34, for example, by hand or robotic, automated or photographic processes well known in the art.

Then as indicated by process blocks 52 and 58, the substrate 29 may be washed with target molecules 26 in the carrier stream 24 where the target molecules 26 are either labeled and binding between the target molecules 26 and the probe molecules 22 detected using conventional SPR.

Alternatively at process box 54 the target molecules 26 and/or the probe molecules 22 may be labeled with fluorescent dye, nanoparticle, or radioactive materials or other tags according to methods known in the art. Reactions of probe molecules 22 with target molecules can be then determined using conventional fluoroscopic or radioactive detecting systems per process block 56.

Optionally then, at process block 58 these readings may be confirmed or augmented through an SPR measurement all using the same substrate 29.

Generally it will be understood that the invention may be used with conventional SPR and/or infrared SPR as will be understood to those of ordinary skill in the art.

It is specifically intended that the present invention not be limited to the embodiments and illustrations contained herein, but include modified forms of those embodiments including portions of the embodiments and combinations of elements of different embodiments as come within the scope of the following claims.

We claim:

1. A method of chemical analysis comprising the steps of:
   (a) preparing a transparent support substrate having a metallic film adhered to a dielectric layer in turn attached to the support substrate, the metallic film having exposed regions surrounded by a hydrophobic material;
   (b) attaching at least one probe molecule to the exposed regions of the metallic film;
   (c) reacting probe molecules attached to the metallic film with a target material in a carrier solution coming into contact with an exposed metallic film surface;
   (d) detecting the reaction using variations in reflectivity caused by surface plasmon resonance; and
   (e) detecting the reaction through sensing of labeling of the target material at different locations.

2. The method of claim 1 wherein the dielectric layer is selected to substantially increase a change in reflectivity caused by surface plasmon resonance for a given amount of reaction.

3. The method of claim 1 wherein the dielectric layer has an index of refraction of 1.3 to 1.7.

4. The method of claim 1 wherein the step of detecting uses a camera forming an image of the substrate over two dimensions.

5. The method of claim 1 wherein the labeling is selected from groups consisting of fluorescent and radioactive labeling.

6. The method of claim 1, further comprising the step of adhering a hydrophobic material to the substrate to expose separated islands of metal.

7. The method of claim 1 wherein the step of detecting the reaction comprises comparing exposed regions of the metallic film to regions covered by the hydrophobic material.

* * * * *

UNITED STATES PATENT AND TRADEMARK OFFICE
CERTIFICATE OF CORRECTION

PATENT NO. : 7,939,345 B2
APPLICATION NO. : 12/015186
DATED : May 10, 2011
INVENTOR(S) : Alastair William Wark et al.

Page 1 of 1

It is certified that error appears in the above-identified patent and that said Letters Patent is hereby corrected as shown below:

IN THE SPECIFICATION:

Column 6, line 47, delete "A" and substitute therefore -- Δ --.

Signed and Sealed this
Twenty-ninth Day of May, 2012

David J. Kappos
*Director of the United States Patent and Trademark Office*